United States Patent [19]
Scheffel et al.

[11] Patent Number: 5,128,495
[45] Date of Patent: Jul. 7, 1992

[54] PROCESS FOR THE PREPARATION OF ALKYLPHOSPHONOUS ACID DIESTERS AND/OR DIALKYLPHOSPHINOUS ACID ESTERS

[75] Inventors: Günter Scheffel, Burghausen; Michael Thiele, Burgkirchen, both of Fed. Rep. of Germany

[73] Assignee: Hoechst Aktiengesellschaft, Frankfurt am Main, Fed. Rep. of Germany

[21] Appl. No.: 504,974

[22] Filed: Apr. 5, 1990

[30] Foreign Application Priority Data

Apr. 7, 1989 [DE] Fed. Rep. of Germany ....... 3911230

[51] Int. Cl.$^5$ .............................. C07F 9/46; C07F 9/48
[52] U.S. Cl. ...................................... 558/134
[58] Field of Search ................... 558/96, 134

[56] References Cited

U.S. PATENT DOCUMENTS

| | | | |
|---|---|---|---|
| 2,903,475 | 8/1959 | Hardwitz | 558/96 |
| 4,032,602 | 6/1977 | Mazour et al. | 558/90 |
| 4,079,103 | 3/1978 | Mazour | 558/90 |
| 4,118,435 | 10/1978 | Kleinstück et al. | 558/90 |

OTHER PUBLICATIONS

Houben-Weyl: "Methoden der organischen Chemie", 4. Aufalge, Band x 11, Teil 2, 1964, hrsg. von E. Müller, p. 18, paragraph 3; pp. 50–51, paragraph 8.
Journal of the Chemical Society, Section C: Organic Chemistry, 1968, pp. 839–842; A. D. Brown et al.:: "Structural effects in reactions of organo phosphorous compounds. II. Reaction of Grignard reagents with phosphonic dichlorides".
Chemical Abstracts, vol. 52, 1958, No. 8070c.
Chemical Abstracts, vol. 54, 1960, No. 18340g.
Chemical Abstracts, vol. 55, 1961, No. 14288f.
Kabachnik, M. I. et al., Chem. Abstr. 52, 8070c (1958).
Sander, M. Chem. Abstr. 54, 18340g (1960).
Kabachnik, M. I. et al., Chem. Abstr. 55, 14288f (1960).

*Primary Examiner*—Mary C. Lee
*Assistant Examiner*—Michael G. Ambrose
*Attorney, Agent, or Firm*—Curtis, Morris & Safford

[57] ABSTRACT

The said compounds are prepared by reaction of trialkyl phosphites with phosphorus trichloride and/or dichlorophosphinous acid monoalkyl esters at −20 to +100° C. and direct subsequent reaction with alkylmagnesium chloride or alkylmagnesium bromide at −60 to +50° C. and subsequent separation of the desired compounds from the distillate of the volatile compounds. Dialkyl alkylphosphonites and monoalkyl dialkylphosphinites are thus obtained without troublesome and expensive purification of intermediates. The phosphorus-containing esters produced are, for their part, useful intermediates, for example for the preparation of flame retardants and plant protection agents.

8 Claims, No Drawings

PROCESS FOR THE PREPARATION OF ALKYLPHOSPHONOUS ACID DIESTERS AND/OR DIALKYLPHOSPHINOUS ACID ESTERS

DESCRIPTION

The invention relates to a process for the preparation of dialkyl alkylphosphonites and/or monoalkyl dialkylphosphinites from the corresponding dialkyl chlorophosphonites or monoalkyl dichlorophosphinites respectively.

The preparation of chlorophosphonous acid diesters or dichlorophosphinous acid monoesters by reaction of phosphorus trichloride with the amounts of a symmetrical trialkyl phosphite necessary to form these esters is known. According to U.S. Pat. No. 4,032,602, the reaction is carried out at $-15°$ to $+75°$ C. in the presence of a water-containing quaternary compound of nitrogen or phosphorus. According to U.S. Pat. No. 4,079,103, the reaction is carried out in the same temperature range in the presence of a polar aprotic solvent. The process according to U.S. Pat. No. 4,118,435 is similar, it also being possible to react dialkyl chlorophosphonites, instead of the symmetrical trialkyl phosphite, with phosphorus trichloride.

M. I. Kabachnik and E. N. Tsvetkov, Doklady Akad. Nauk. S.S.S.R 117 (1957), pages 817 to 820 (C.A. 52/8070c) describe the preparation of alkylphosphonous acid diesters by reaction of chlorophosphonous acid diesters with alkylmagnesium halide, for example methylmagnesium iodide, in diethyl ether at $-60°$ to $-65°$ C.

According to M. Sander, Ber. 93, page 1220 et seq. (C.A. 54/18340g), dialkylphosphinous acid monoesters are obtained by reaction of dichlorophosphinous acid monoesters with 2 moles of alkylmagnesium chloride in diethyl ether at $-50°$ to $+35°$ C., it being essential to add the ethereal solution of the alkylmagnesium chloride at such a rate that an excess of dichlorophosphinous acid monoester is always present in the reaction vessel during the addition. Alkylmagnesium bromides give poor yields or no yields at all.

For the reaction with alkylmagnesium chlorides, it is important that very pure chlorophosphonous acid diesters or dichlorophosphinous acid monoesters are used, the purification of these substances requiring three to four distillations and therefore being time-consuming and uneconomical (Ber. 93, page 1222, paragraph 2).

M. I. Kabachnik and E. N. Tsvetkov, Doklady Akad. Nauk. S.S.S.R 135 (1960), pages 323 to 326 (C.A. 55/14288f) carry out the reaction using alkylmagnesium bromide or chloride in the presence of pyridine, an improvement in yield being obtained. However, they report that the dimethylphosphinous acid monoesters cannot be prepared in this manner.

It is the object of the present invention to make available a process with which it is possible to prepare dialkyl alkylphosphonites or monoalkyl dialkylphosphinites or mixtures of the two last-mentioned compounds from symmetrical trialkyl phosphite by reaction with dichlorophosphinous acid monoesters or with phosphorus trichloride or with mixtures of the two last-mentioned compounds and subsequent reaction with alkylmagnesium chloride or bromide without troublesome purification of intermediates, the production of dialkyl methylphosphonites or monoalkyl dimethylphosphinites or mixtures of the two last-mentioned compounds also being possible.

The novel process for the preparation of at least one compound of the formula $$R_nP(OR')_{3-n} \qquad (1)$$

in which
R is an alkyl group having 1 to 4 carbon atoms, a vinyl group or an allyl group,
R' is an alkyl group having 1 to 4 carbon atoms, a chloroalkyl group having 2 to 4 carbon atoms or a bromoalkyl group having 2 to 4 carbon atoms and
$n=1$ or 2 by reacting at least one compound which is selected from the group comprising compounds of the formulae $PCl_3$ (2), $Cl_2POR'$ (3) and mixtures of these compounds, with a compound of the formula $$P(OR')_3 \qquad (4)$$

where R' in the formulae (3) and (4) has the abovementioned meaning, after completion of this reaction reacting the reaction product or the reaction products of the formula $$Cl_nP(OR')_{3-n} \qquad (5)$$

in which R' and n have the abovementioned meaning, with a compound of the formula $$XMgR \qquad (6)$$

in which X is Cl or Br and R has the abovementioned meaning, then separating off the resulting compounds of the formula (I) from the reaction mixture by distillation, comprises bringing 0.5 to 2.1 moles of the compound (4) per mole of the compound (2) and/or 0.1 to 1.1 moles of the compound (4) per mole of the compound (3) to reaction at $-20°$ to $+100°$ C., adjusting the temperature to $-60°$ to $+50°$ C. after completion of the reaction, bringing the reaction mixture into contact, without prior separation and purification of a reaction product, with 1 to 1.1 moles of a compound (6), which is substantially present in solution, per g atom of chlorine bonded to phosphorus in the reaction mixture of the compound (4) with the compound (2) or the compound (3) or mixtures of the two last-mentioned compounds while maintaining the set temperature and mixing intensively, then maintaining the set temperature, or adjusting it to 10° to 30° C., for 0 to 3 hours and then separating off the compound(s) (1) formed.

The novel process comprises two different reactions which are carried out successively in the same reaction space. First 0.5 to 2.1 moles of trialkyl phosphite of the formula (4) are brought to reaction per mole of phosphorus trichloride. More than 2.1 moles of trialkyl phosphite can also be used, but this in general increases the subsequent expenditure on distillation. The trialkyl phosphite may contain 1 to 4 carbon atoms in the alkyl groups, or chloroalkyl groups having 2 to 4 carbon atoms or bromoalkyl groups having 2 to 4 carbon atoms. Preferably, a trialkyl phosphite is used in which the alkyl groups each contain 1 to 4 carbon atoms or which contains 2-chloroethyl groups. The alkyl group may be straight-chain or branched. If the trialkyl phosphite contains haloalkyl groups, the halogen may be bonded to any carbon atom apart from the carbon atom which is bonded to oxygen. Although it is also possible on the one hand to employ mixtures of various trialkyl phosphites of the formula (4) and on the other hand mixtures of phosphorus trichloride and dichlorophosphinous acid monoesters, preferably only one compound of the two reaction components is used in each case.

Instead of phosphorus trichloride, the monoalkyl dichlorophosphinites of the formula (3) can advantageously be employed, and in this case 0.1 to 1.1 moles of trialkyl phosphite of the formula (4), as described in more detail above, are reacted per mole of monoalkyl dichlorophosphinite of the formula (3). In a preferred embodiment of the process according to the invention, those monoalkyl dichlorophosphinites (3) are used which are produced by reaction of 1 mole of phosphorus trichloride with 1 to 1.5 moles, preferably 1 to 1.2 moles, of an alkanol of the formula R'OH, the hydrogen chloride formed being separated off by driving off by lowering the pressure and/or with inert gas, for example nitrogen, or by salt formation, for example with a tertiary amine. An excess of up to 0.5 moles of alkanol per mole of phosphorus trichloride leads to proportionate formation of chlorophosphonous acid diesters, the proportion of which is expediently allowed for in the following reaction with trialkyl phosphite. In the formula R'OH, R' is an alkyl group having 1 to 4 carbon atoms, or a chloroalkyl group having 2 to 4 carbon atoms or a bromoalkyl group having 2 to 4 carbon atoms, in which the halogen atom is not bonded to the carbon atom which carries the OH group.

If it is intended to prepare monoalkyl dialkylphosphinites, which are compounds of the formula (1) in which n is 2, 0.5 mole of trialkyl phosphite (4) is advantageously reacted per mole of phosphorus trichloride (2). If it is intended to prepare dialkyl alkylphosphonites, which are compounds of the formula (1) in which n=1, 2 to 2.1 moles of trialkyl phosphite (4) per mole of phosphorus trichloride (2) or 1 to 1.1 moles of trialkyl phosphite (4) per mole of dichlorophosphinous acid ester (3) are advantageously reacted. If an amount of trialkyl phosphite which is between 0.5 and 2.0 moles of trialkyl phosphite is employed per mole of phosphorus trichloride, mixtures of monoalkyl dichlorophosphinite and dialkyl chlorophosphonite are obtained, the mixture ratio of which results from the amount of trialkyl phosphite used. The same applies if an amount of trialkyl phosphite which is between 0.1 and 1 mole is used per mole of monoalkyl dichlorophosphinite. It may be advantageous to prepare mixtures of this type first, then to react these, as described subsequently, with a corresponding amount of a compound of the formula XMgR (6) and then to separate the mixture of monoalkyl dialkylphosphinite and dialkyl alkylphosphonite resulting from this reaction into the individual components, for example by fractional distillation.

The reaction of the trialkyl phosphite (4) with phosphorus trichloride (2) and/or the monoalkyl dichlorophosphinites (3) is carried out at a temperature of $-20°$ to $100°$ C. Above $100°$ C., too many troublesome side reactions in general occur, which lead to undesired products and thus to losses in yield; under $-20°$ C., the rate of reaction is in general unnecessarily slow. Expediently, if compounds are employed in which R' is a methyl or ethyl group, lower reaction temperatures are chosen than with those compounds in which R' is an alkyl group having 3 to 4 carbon atoms. Preferably, reaction temperatures of $20°$ to $50°$ C. are used. Good results are obtained if polar aprotic solvents, as are described in U.S. Pat. No. 4,079,103 are added during the reaction.

In a preferred embodiment of the process according to the invention, the reaction of the compounds of the formulae $PCl_3$ (2) or $Cl_2POR'$ (3) or of mixtures of these two with the compound of the formula $P(OR')_3$ (4) is carried out in the presence of 1 to 10% by weight, based on the total of the compounds $PCl_3 + Cl_2POR' + P(OR')_3$, of at least one compound of the formula

in which
Y is alkyl having 1 to 6 carbon atoms, phenyl or $NR_2$ and
R is alkyl having 1 to 4 carbon atoms, where $R_2$ may also be a 1,4-butylene radical.

Particularly preferentially, 3 to 6% by weight of the compounds mentioned are used. Particularly good results are obtained using phosphoric acid tri(dimethylamide).

The sequence in which the compounds of the formulae $PCl_3$ or $Cl_2POR'$ and also their mixtures, as one component, and $P(OR')_3$, as the other component, are used is not critical, but the aprotic polar solvent should be present in a mixture with the initially introduced component and the addition of the other component should be carried out with mixing, for example by stirring, in such a way that no substantial deviations from the chosen reaction temperature, for example owing to sudden local heating, occur. After the two reactants have been added together, a post-reaction time of 5 to 60 minutes may be useful, but it is not necessary in all cases.

The reaction mixture of $PCl_3$ (2) or $Cl_2POR'$ (3) or their mixtures and $P(OR')_3$ (4), prepared as described in the above sections, is reacted according to the invention, without isolation of reaction products of the formula $Cl_nP(OR')_{3-n}$ (5), in which R' and n have the meaning given further above, with a compound of the formula XMgR (6), in which X is Cl or Br and R has the abovementioned meaning. Advantageously, before addition of the compound of the formula XMgR (6), 2 to 15 parts by weight of an anhydrous aprotic solvent whose boiling point is at least $20°$ C. above the boiling point of the highest-boiling compound of the formula $R_nP(OR')_{3-n}$ (1), which it is intended to prepare, are added to the reaction mixture of the phosphorus-containing compounds, per 1 part by weight of this mixture. The anhydrous aprotic solvent should be liquid at $+50°$ C., preferably at $+15°$ C. The upper limit on the boiling point of the aprotic solvent is determined by the fact that, in the later removal of the compound(s) of the formula (1) by distillation, the bottom temperature should not exceed the thermal capacity of these compounds. In general, the boiling point of the aprotic solvent at 133 Pa should not exceed $60°$ to $150°$ C., depending on the compound of the formula (1) produced. The addition of the solvent is expediently carried out after the completion of the reaction of the phosphorus-containing compounds, but it can also be carried out entirely or partially during or before this reaction, in particular if the maintenance of the stirrability of the suspension necessitates it. Preferably, 4 to 10 parts by weight of the anhydrous aprotic solvent are employed per part of reaction product.

Suitable aprotic solvents are, for example, relatively high-boiling hydrocarbons and ethers, such as toluene, xylene, tetralin, decalin, di-n-propyl ether, dibutyl ether, the dimethyl and diethyl ethers of ethylene glycol and diethylene glycol, triethylene glycol dimethyl ether and tetraethylene glycol dimethyl ether. The choice of a suitable aprotic solvent may be illustrated by the following examples: if it is intended to produce methyl dimethylphosphinite, which has the lowest boiling point (56.7° C. at 98 kPa) of all products which can be prepared according to the invention, di-n-propyl ether (boiling point 90° C. at 98 kPa) is suitable as the aprotic solvent. This solvent would also be suitable for the methylmagnesium chloride or bromide necessary for the preparation of the abovementioned phosphinous acid ester. If isobutyl dimethylphosphinite (boiling point 132° C. at 98 kPa) is intended to be produced, diethylene glycol dimethyl ether (boiling point 162° C. at 98 kPa), for example, would be suitable as the aprotic solvent to be added, the distillation expediently being carried out under reduced pressure in order to keep the thermal loading of the distillation bottom as small as possible. For the preparation of diisobutyl methylphosphonite (boiling point 39 to 40° C. at 133 Pa), tetraethylene glycol dimethyl ether (boiling point 78° C. at 133 Pa), for example, would be suitable.

The reaction mixture of the phosphorus-containing compounds is adjusted to a temperature of −60° to +50° C. before it comes into contact with the compound of the formula XMgR (6). Under −60° C., the subsequent reaction in general proceeds too slowly; above +50° C., undesired side reactions occur, for example, depending on the number of carbon atoms, ester bonds can be cleaved, compounds of pentavalent phosphorus and phosphines being formed. Preferably, the phosphorus-containing reaction mixture is brought to a temperature of −20° to +20° C., the temperatures preferably being adjusted to the lower values in the case of methyl and ethyl esters. Per g atom of chlorine bonded to phosphorus present in the reaction mixture of the compound (4) with the compound (2) or the compound (3), 1 to 1.1 moles of a compound of the formula XMgR (6), which is substantially present in solution, are then brought into contact with the reaction mixture. Advantageously, 1 to 1.05 moles of a compound of the formula XMgR (6) which is substantially present in solution are employed. During the reaction, the preset temperature should be approximately maintained by an appropriate rate of addition and cooling. Intensive mixing of the reacting components, for example by rapid turbulent stirring, substantially increases the yield of the desired compound of the formula $R_nP(OR')_{3-n}$ (1).

In general, the solution of the compound XMgR (6) will be introduced slowly into the mixture of the phosphorus-containing compounds, but the reverse procedure, initial introduction of the solution of the compound XMgR (6) followed by introduction of the reaction mixture of the phosphorus-containing compounds, is also possible. Suitable solvents for the compound XMgR are primarily ethers, such as diethyl ether, diisopropyl ether, di-n-propyl ether or dibutyl ether, solutions in tetrahydrofuran preferably being employed owing to the good solubility and action. Furthermore, compounds of the formula XMgR preferably used are those in which R is methyl or ethyl. Compounds of the formula XMgR in which X is chlorine are also preferred.

If it is intended to prepare compounds of the formula $R_nP(OR')_{3-1}$ (1) which contain lower alkyl radicals R and/or R', for example methyl or ethyl, it is recommended to carry out the reaction with the compound of the formula XMgR in the lower temperature range, that is between −60° and +20° C.; if it is intended to prepare compounds of the formula (I) containing higher alkyl radicals, the higher temperature range from about 0° to +50° C. is expediently selected.

After the total amount of the compound XMgR has been brought into contact with the phosphorus-containing reaction mixture, the separation of the desired compounds of the formula (1) can be begun. Frequently it is advantageous, before separation of these compounds, additionally to use a post-reaction time of up to 3 hours, preferably up to 1 hour, during which the temperature is either kept at the value originally set or adjusted to 10° to 30° C.

In some cases, it may be expedient, after addition of the compound XMgR, to add a further compound which forms a complex with the compound $MgX_2$ formed during the reaction, for example pyridine or dioxane. Especially when alkylmagnesium bromides are used, this can contribute to increasing the yield of the desired compounds of the formula $R_nP(OR')_{3-n}$ (1).

After completion of the reaction between the compound XMgR and the phosphorus-containing reaction mixture and, if appropriate, a post-reaction time, all of the volatile substances are expediently first removed from the reaction mixture by distillation, in which case, depending on the reactants employed, a bottom temperature of +60° to 150° C. should not be exceeded, and in the case of compounds containing lower alkyl radicals the lower bottom temperatures must again also be selected. Reduced pressure is expediently used in the distillation of compounds of the formula (1) having a relatively high boiling point in order as far as possible to remove all fractions of the compound of the formula (1) from the reaction mixture at as low a bottom temperature as possible. In some cases it may be advantageous to separate off precipitated solid components from the reaction mixture, for example by filtration, before beginning with the removal of the volatile components by distillation. The mixture of all volatile components obtained after the distillation is then separated into the individual components by fractional distillation in the customary manner, it being possible to re-use non-reacted reactants, the solvent for the compound XMgR, and also the aprotic solvent which is added to the reaction mixture of the phosphorus-containing compounds before addition of the compound XMgR. One or two fractions are obtained which principally contain monoalkyl dialkylphosphinites, dialkyl alkylphosphonites or both. They can be purified further by renewed fractional distillation, as required. In some cases, the mixture of the solvents and phosphorus-containing compounds removed by distillation can be used for further reactions without purification.

The two reactions carried out successively in the same reaction space according to the invention are performed with the exclusion of oxygen and substantial exclusion of water (moisture) using reagents which are as dry as possible, in a dry atmosphere, for example nitrogen. The same also applies to the working up of the reaction mixture.

The dialkyl alkylphosphonites or monoalkyl dialkylphosphinites prepared according to the invention are useful intermediates for the preparation of, for example, flame retardants or plant protection agents.

As already mentioned further above, the process according to the invention makes it possible to prepare dialkyl alkylphosphonites and monoalkyl dialkylphosphinites without troublesome and expensive purification of intermediates, the commercially important methyl compounds, in particular, also being obtainable in good yield.

The following examples are intended to illustrate the invention in more detail.

EXAMPLE 1

A 4-necked flask fitted with a thermometer, stirrer, gas inlet tube and an attachment which contains a dropping funnel and a tube for leading off gas, is flushed with dry nitrogen and kept under a gentle stream of nitrogen during the reactions described below. 47.4 g (=0.28 mole) of triethyl phosphite (98% pure) and 2.2 g of hexamethylphosphoramide are then initially introduced. 19.6 g of phosphorus trichloride (98% pure=0.14 mole) are then introduced dropwise into the flask, with stirring, in the course of 20 min and, by means of cooling, the temperature, which rises during the reaction, is kept at +40° C., the mixture is then stirred for a further 1 hour, the contents of the flask cooling to +20° C. −2 mole of triethyl phosphite and 3.3% by weight of hexamethylphosphoramide, based on the total of phosphorus trichloride and triethyl phosphite, are used per mole of phosphorus trichloride.

The temperature of the contents of the flask is lowered to −20° C. 283 g of diethylene glycol dimethyl ether which has been dried over metallic sodium and distilled are then added, the dropping funnel is replaced, and distillation device suitable for vacuum operation is connected to the attachment, the receiver of said device being cooled with a mixture of acetone and solid carbon dioxide. While keeping at −20° C., 129 g of a solution which contains 25.4% by weight of methylmagnesium chloride in tetrahydrofuran are introduced dropwise, with turbulent stirring, precipitating magnesium chloride remaining dispersed in the reaction mixture. After completion of the dropwise addition, the cooling for the flask is removed and the flask is stirred during the course of 1 hour while warming to +20° C. −4.3 parts by weight of diethylene glycol dimethyl ether (b.p. at 98 kPa about 162° C.) per part by weight of the reaction mixture of triethyl phosphite and phosphorus trichloride and 1.05 moles of methylmagnesium chloride per g atom of chlorine bonded to phosphorus are used.

After the post-reaction time has elapsed, the pressure in the reaction apparatus is reduced to 2 kPa, the lowest-boiling components of the contents of the flask passing over into the distillation receiver. The temperature of the contents of the flask is then slowly increased to 65° C. (to the boiling point of the diethylene glycol dimethyl ether at the pressure used) and this temperature is maintained for as long as the contents of the flask still remain stirrable. The distillation is then ended.

300.9 g of distillate are obtained which, according to nuclear magnetic resonance spectral analysis (NMR), has the following composition:
50.1 g of $CH_3P(OC_2H_5)_2$ (b.p. at 98 kPa about 116° C.)
3.8 g $P(OC_2H_5)_3$
0.8 g $(CH_3)_2P(OC_2H_5)$
0.2 g $(CH_3)_3P$
96.0 g tetrahydrofuran
150.0 g diethylene glycol dimethyl ether Based on the trivalent phosphorus contained in the compounds $P(OC_2H_5)_3$ and $PCl_3$ employed, the yield of $CH_3P(OC_2H_5)_2$ is 87.1%.

The distillate obtained can fractionated without noticeable losses, $P(OC_2H_5)_3$ being recovered. Taking into account the recovered starting material, the yield of $CH_3P(OC_2H_5)_2$, based on trivalent phosphorus employed, is 92.1%.

The distillate can be used without further purification for chemical reactions for the preparation, for example, of plant protection agents or flame retardants.

EXAMPLE 2

The procedure is as described in Example 1, with the following changes:
52.5 g of $P(OCH_3)_3$ (98% pure=0.415 mole) and 3.4 g of hexamethylphosphoramide are initially introduced, 73.5 g of dichloroisobutoxy-phosphane $Cl_2POC_4H_9$-iso (98% pure=422 mole) are added dropwise at a constantly maintained +50° C., the mixture is kept at +50° C. for 1 hour with stirring and cooled to −20° C., 325 g of diethylene glycol dimethyl ether are added, 251.5 g of solution which contains 25.4% by weight of $CH_3MgCl$ (=63.88 g =0.854 mole) in tetrahydrofuran are added dropwise at −20° C., the mixture is stirred for a further 1 hour, during which time it warms to +20° C., and distilled as described in Example 1.

The following are used:
0.98 mole of $P(OCH_3)_3$ per mole of $Cl_2POC_4H_9$-iso.
2.7% by weight of hexamethylphosphoramide, based on $Cl_2POC_4H_9$-iso + $P(OCH_3)f_2$ mixture.
2.6 parts by weight of diethylene glycol dimethyl ether per part by weight of the mixture described above and 1.01 mole of $CH_3MgCl$ per g atom of chlorine bonded to phosphorus.

471 g of distillate of the following composition are obtained:
32.9 g of $CH_3P(OCH_3)_2$ (b.p. at 98 kPa about 88° C.)
45.0 g of $CH_3P(OCH_3)(OC_4H_9$-iso)
12.3 g of $P(OCH_3)_3$
1.9 g of $(CH_3)_2P(OCH_3)$
2.8 g of $(CH_3)_2POC_4H_9$-iso
187.0 g of tetrahydrofuran
190.0 g of diethylene glycol dimethyl ether Yield of $CH_3P(OCH_3)_2 + CH_3P(OCH_3)(OC_4H_9$-iso), based on trivalent phosphorus employed: 72.2%.

Taking into account the recoverable $P(OCH_3)_3$: 81.9%.

EXAMPLE 3

The procedure is as described in Example 1, with the following changes: 52.5 g of $P(OCH_3)_3$ (98% pure=0.415 mole) and 2.3 g of hexamethylphosphoramide are initially introduced, 28.4 g of $PCl_3$ (98% pure=0.203 mole) are added dropwise at a constantly maintained +40° C., the mixture is kept at +40° C. for 1 hour, with stirring, and cooled to +20° C., 307 g of triethylene glycol dimethyl ether (b.p. at 98 kPa about 226° C.) are added, 293.5 g of solution which contains 24.7% by weight of $C_4H_9MgCl$ (=72.49 g=0.6202 mole) in tetrahydrofuran are added dropwise at +20° C., the mixture is stirred for a further 2 hours and distilled as described in Example 1, the flask contents being heated to 110° C. (to the boiling point of the triethylene glycol dimethyl ether at 266 Pa pressure).

The following are used:
2.045 mole of P(OCH$_3$)$_3$ per mole of PCl$_3$.
2.7% by weight of hexamethylphosphoramide, based on PCl$_3$+P(OCH$_3$)$_3$ mixture.
3.8 parts by weight of triethylene glycol dimethyl ether per part by weight of the mixture described and 1.02 mole of C$_4$H$_9$MgCl per g atom of chlorine bonded to phosphorus.
337.3 g of distillate of the following composition are obtained:
71.4 g of C$_4$H$_9$P(OCH$_3$)$_2$(b.p. at 98 kPa about 157° C.)
13.2 g of (C$_4$H$_9$)$_2$POCH$_3$(b.p. at 98 kPa about 201° C.)
221.0 g of tetrahydrofuran
31.9 g of triethylene glycol dimethyl ether
Yield of C$_4$H$_9$P(OCH$_3$)$_2$, based on trivalent phosphorus employed: 76.9%.
Taking into account the likewise utilizable (C$_4$H$_9$)$_2$POCH$_3$: 89.%.

EXAMPLE 4

The procedure is as described in Example 1, with the following changes:
15.3 g of Cl$_2$POCH$_3$ (97.5% pure=0.112 mole), which has been obtained from the reaction of PCl$_3$ with CH$_3$OH with removal of HCl, and 1 g of hexamethylphosphoramide are initially introduced, 14.2 g of P(OCH$_3$)$_3$ (98% pure=0.112 mole) are added dropwise at a constantly maintained +40° C., the mixture is kept at +40° C. for 1 hour, with stirring, and cooled to −20° C., 100 g of diethylene glycol dimethyl ether are added, 91.4 g of solution which contains 30% by weight of CH$_3$MgBr (=27.43 g=0.23 mole) dissolved in tetrahydrofuran are added dropwise at −20° C. in the course of 1 hour, and the mixture is stirred for a further hour while warming to +20° C. and distilled as described in Example 1.
The following are used:
1 mole of P(OCH$_3$)$_3$ per mole of Cl$_2$POCH$_3$.
3.4% by weight of hexamethylphosphoramide, based on Cl$_2$POCH$_3$+P(OCH$_3$)$_3$ mixture.
3.4 parts by weight of diethylene glycol dimethyl ether per part by weight of the mixture described above and 1.025 mole of CH$_3$MgBr per g atom of chlorine bonded to phosphorus.
122 g of distillate of the following composition are obtained
15 2 g of CH$_3$P(OCH$_3$)$_2$ (b.p. at 98 kPa about 88° C.)
1.8 g of (CH$_3$)$_2$POCH$_3$ (b.p. at 98 kPa about 57° C.)
0.25 g of P(OCH$_3$)$_3$
1.1 g of (CH$_3$)$_3$P
1.6 g of (CH$_3$)$_3$PO
63.5 g of tetrahydrofuran
38.5 g of diethylene glycol dimethyl ether
Yield of CH$_3$P(OCH$_3$)$_2$, based on trivalent phosphorus employed: 73.8%.
Taking into account the recoverable P(OCH$_3$)$_3$: 74.5%.

EXAMPLE 5

The procedure is as described in Example 1, with the following changes:
56.0 g of PCl$_3$ (98% pure=0.4 mole) and 3.5 g of hexamethylphosphoramide are initially introduced, 43.8 g of P(OH$_3$H$_7$-iso)$_3$(95% pure=0.2 mole) are added dropwise at a constantly maintained +40° C., the mixture is kept at +40° C. for a total of 2 hours, with stirring, and cooled to +40° C., 300 g of diethylene glycol dimethyl ether are added, 341 g of solution which contains 26.4% by weight of CH$_3$MgCl (−90 g=1.2 mole) dissolved in tetrahydrofuran are added dropwise at −40° C., then 258 g of dioxane are added, the mixture is warmed to +20° C. with stirring, the finely crystalline precipitate of the resulting magnesium chloride-dioxane addition compound is filtered off with the exclusion of air and moisture, the filter cake is washed with 52 g of dioxane and the filtrate is distilled as described in Example 1.
The following are used:
0.5 mole of P(OC$_3$H$_7$-iso)$_3$ per mole of PCl$_3$.
3.5% by weight of hexamethylphosphoramide, based on PCl$_3$ +P(OC$_3$H$_7$-iso)$_3$ mixture.
3 parts by weight of diethylene glycol dimethyl ether per part by weight of the mixture described above and 1 mole of CH$_3$MgCl per g atom of chlorine bonded to phosphorus.
573.5 g of distillate of the following composition are obtained:
52.6 g of (CH$_3$)$_2$POC$_3$H$_7$-iso (b.p. at 98 kPa about 90° C.)
10.0 g of CH$_3$P(OC$_3$H$_7$-iso)$_2$ (b.p. at 98° C. kPa about 139° C.)
1 9 g of (CH$_3$)$_3$P
1.5 g of (CH$_3$)$_3$PO
88.5 g of dioxane
251.0 g of tetrahydrofuran
168.0 g of diethylene glycol dimethyl ether
Yield of (CH$_3$)$_2$POC$_3$H$_7$-iso, based on trivalent phosphorus employed: 73.1%.
Together with the likewise utilizable CH$_3$P(OC$_3$H$_7$-iso)$_2$, the yield, based on trivalent phosphorus, is: 83.3%.

EXAMPLE 6

The procedure is as described in Example 1, with the following changes:
26.2 g of P(OCH$_3$)$_3$ (98% pure=0.207 mole) and 1.6 g of hexamethylphosphoramide are initially introduced, 29.0 g of PCl$_3$(98% pure=0.207 mole) are added dropwise in the course of 0.25 hour at a constantly maintained +40° C., the mixture is stirred at +40° C. for a further hour and cooled to −60° C., 472 g of diethylene glycol dimethyl ether are added, 183 g of solution which contains 26% by weight of CH$_3$MgCl (=72.49 g =0.6202 mole) in tetrahydrofuran are added dropwise at −60° C. and the mixture is stirred further while warming to +20° C. (total time 2 hours) and distilled as described in Example 1.
The following are used:
1 mole of P(OCH$_3$)$_3$ per mole of PCl$_3$.
2.9% by weight of hexamethylphosphoramide, based on PCl$_3$ +P(OCH$_3$)$_3$ mixture.
8.5 parts by weight of diethylene glycol dimethyl ether per part by weight of the mixture described above and 1.02 mole of CH$_3$MgCl per g atom of chlorine bonded to phosphorus.
487 g of distillate of the following composition are obtained:
22.0 g of CH$_3$P(OCH$_3$)$_2$ (b.p. at 98 kPa about 88° C.)
12.6 g of (CH$_3$)$_2$POCH$_3$
1.4 g of P(OCH$_3$)$_3$
1.3 g of (CH$_3$)$_3$P
135.0 g of tetrahydrofuran
314.7 g of diethylene glycol dimethyl ether
Yield of CH$_3$P(OCH$_3$)$_2$+(CH$_3$)$_2$POCH$_3$, based on trivalent phosphorus employed: 81.9%.

Taking into account the recoverable $P(OCH_3)_3$: 84.3%.

We claim:

1. A process for the preparation of at least one compound of the formula $$R_nP(OR')_{3-n} \qquad (1)$$

in which
R is an alkyl group having 1 to 4 carbon atoms, a vinyl group or an allyl group,
R' is an alkyl group having 1 to 4 carbon atoms, a chloroalkyl group having 2 to 4 carbon atoms or a bromoalkyl group having 2 to 4 carbon atoms and =1 or 2 by reacting at least one compound which is selected from the group consisting of compounds of the formulae $PCl_3$ (2), $Cl_2POR'$ (3) and mixtures of these compounds with a compound of the formula $$P(OR')_3 \qquad (4)$$

R' in the formulae (3) and (4) has the abovementioned meaning, after completion of this reaction, reacting the reaction product or the reaction products of the formula $$Cl_nP(OR')_{3-n} \qquad (5)$$

in which R' and n have the abovementioned meaning, with a compound of the formula $$XMgR \qquad (6)$$

in which X is Cl or Br and R has the abovementioned meaning, and then separating off the resulting compounds of the formula (1) from the reaction mixture by distillation, which comprises bringing 0.5 to 2.1 moles of the compound (4) per mole of the compound (2) or 0.1 to 1.1 moles of the compound (4) per mole of the compound (3) to reaction at $-20°$ to $+100°$ C., adjusting the temperature to $-60°$ to $+50°$ C. after completion of the reaction, bringing the reaction mixture into contact, without prior separation and purification of a reaction product, with 1 to 1.1 moles of a compound (6), which is substantially present in solution, per g atom of chlorine bonded to phosphorus in the reaction mixture of the compound (4) with the compound (2) or the compound (3) or mixtures of the two last-mentioned compounds while maintaining the set temperature and mixing intensively, then maintaining the set temperature, or adjusting it to 10° to 30° C., for 0 to 3 hours and then separating off the compound(s) (1) formed.

2. The process as claimed in claim 1, wherein 2 to 15 parts by weight of an anhydrous aprotic solvent whose boiling point is at least 20° C. above the boiling point of the highest-boiling compound $R_nP(OR')_{3-n}$ to be prepared are added per 1 part by weight of the reaction mixture of at least one compound of the formulae $PCl_3$ or $Cl_2POR'$ or mixtures of these with the compound $P(OR')_3$, before said mixture comes into contact with the compound XMgR.

3. The process as claimed in claim 1, wherein the reaction of at least one compound of the formulae $PCl_3$ or $Cl_2POR'$ or mixtures of these with the compound of the formula $P(OR')_3$ is carried out in the presence of 1 to 10% by weight, based on the total of the compounds $PCl_3 + Cl_2POR' + P(OR')_3$, of at least one compound of the formula

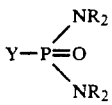

(7)

in which
Y is alkyl having 1 to 6 carbon atoms, phenyl or $NR_2$ and
R is alkyl having 1 to 4 carbon atoms, where $R_2$ may also be a 1,4-butylene radical.

4. The process as claimed in claim 1, wherein a compound of the formula $P(OR')_3$ is employed in which R' is an alkyl group having 1 to 4 carbon atoms or a 2-chloroethyl group.

5. The process as claimed in claim 1, wherein a compound of the formula XMgR is employed in which X is Cl or Br and R is methyl or ethyl.

6. The process as claimed in claim 1, wherein the compound of the formula XMgR is dissolved in tetrahydrofuran.

7. The process as claimed in claim 1, wherein the reaction of at least one compound of the formulae $PCl_3$ or $Cl_2POR'$ or mixtures of these with $P(OR')_3$ is carried out at a temperature of $+20°$ to $+50°$ C.

8. The process as claimed in claim 1, wherein the reaction of the compound of the formula XMgR with the reaction mixture of at least one compound of the formulae $PCl_3$ or $Cl_2POR'$ or mixtures of these with $P(OR')_3$ is carried out at a temperature of $-20°$ to $+20°$ C.

* * * * *